(12) United States Patent
Teague et al.

(10) Patent No.: US 9,950,037 B2
(45) Date of Patent: Apr. 24, 2018

(54) ENHANCING PROGENITOR CELL NUMBERS

(71) Applicants: The Board of Regents of the University of Oklahoma, Norman, OK (US); Oklahoma Medical Research Foundation, Oklahoma City, OK (US)

(72) Inventors: Tracy Kent Teague, Tulsa, OK (US); Jonathan D. Wren, Norman, OK (US); Siva Kumar Gandhapudi, Oklahoma City, OK (US); Julie Harris Marino, Tulsa, OK (US); Chibing Tan, Broken Arrow, OK (US); Ashlee Allison Rempel, Tulsa, OK (US); Charles Justin Van De Wiele, Tulsa, OK (US)

(73) Assignees: The Board of Regents of the University of Oklahoma, Norman, OK (US); Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 14/947,722

(22) Filed: Nov. 20, 2015

(65) Prior Publication Data
US 2016/0143997 A1 May 26, 2016

Related U.S. Application Data

(60) Provisional application No. 62/082,816, filed on Nov. 21, 2014.

(51) Int. Cl.
*A61K 38/20* (2006.01)
*A61K 35/28* (2015.01)

(52) U.S. Cl.
CPC .............. *A61K 38/20* (2013.01); *A61K 35/28* (2013.01); *A61K 38/2046* (2013.01)

(58) Field of Classification Search
None
See application file for complete search history.

(56) References Cited

PUBLICATIONS

Kapucu et al, Asia-Pacific Journal of Oncology Nursing, 2014; vol. 1, No. 1.*
"Stem Cell Transplant for Cancer", American Cancer Society, 2016.*
Ogura et al, Blood, 2001, vol. 98, pp. 2101-2107.*
Ito et al, International Immunology, 2006; vol. 18, No. 8, pp. 1253-1263.*
Bourdeau et al, Stem Cells, Feb. 2013; vol. 31, pp. 293-304.*
Tan et al, The Journal of Immunology, 2011; vol. 186, Issue 1, Supplement, 64.7.*
Wang, S.D., et al.; "Sepsis-induced apoptosis of the thymocytes in mice."; J Immunol; vol. 152; 1994; 5014-5021.
Vonfreeden-Jeffrey, U., et al.; "Lymphopenia in Interleukin (IL)-7 Gene-deleted Mice Identifies IL-7 as a Nonredundant Cytokine"; J. Exp. Med.; vol. 181; Apr. 1995; 1519-1526.
Okamura, H., et al.; "Cloning of a new cytokine that induces IFN-y production by T cells"; Nature; vol. 378; Nov. 2, 1995; 88-91.
Dao, T., et al.; "Interferon-y-Inducing Factor, a Novel Cytokine, Enhances Fas Ligand-Mediated Cytotoxicity of Murine T Helper 1 Cells"; Cellular Immunology; vol. 173; 1996; 230-235.
Maki, K., et al.; "Interleukin 7 receptor-deficient mice lack yo T cells"; Proc. Natl. Acad. Sci. USA; vol. 93; Jul. 1996; 7172-7177.
Takeda, K. et al.; "Defective NK Cell Activity and Th1 Response in IL-18-Deficient Mice"; Immunity; vol. 8; Mar. 1998; 383-390.
Hoshino, K. et al.; "Cutting Edge: Generation of IL-18 Receptor-Deficient Mice: Evidence for IL-1 Receptor-Related Protein as an Essential IL-18 Binding Receptor"; J Immunol; vol. 162; 1999; 5041-5044.
Hoshino, K., et al.; "IL-13 Production by NK Cells: IL-13-Producing NK and T Cells Are Present In Vivo in the Absence of IFN-y"; J Immunol; vol. 162; 1999; 51-59.
Okamoto, I., et al.; "Development of CD8+ Effector T Cells Is Differentially Regulated by IL-18 and IL-12"; J Immunol; vol. 163; 1999; 3202-3211.
Teague, T.K., et al.; "Activation-induced Inhibition of Interleukin 6-mediated T Cell Survival and Signal Transducer and Activator of Transcription 1 Signaling"; J. Exp. Med.; vol. 191, No. 6; Mar. 20, 2000; 915-925.
Yoshimoto, T., et al.; "IL-18 induction of IgE: dependence on CD4+ T cells, IL-4 and STAT6"; Nature Immunology; vol. 1, No. 2; Aug. 2000; 132-137.
Hoshino, T., et al.; "Cutting Edge: IL-18-Transgenic Mice: In Vivo Evidence of a Broad Role for IL-18 in Modulating Immune Function"; J Immunol; vol. 166; 2001; 7014-7018.
Nakanishki, K., et al.; "Interleukin-18 Regulates Both TH1 and TH2 Responses"; Annu. Rev. Immunol.; vol. 19; 2001; 423-474.
Ogura, T., et al.; "Interleukin-18 stimulates hematopietic cytokine and growth factor formation and augments circulating granulocytes in mice"; Blood; vol. 98, No. 7; Oct. 1, 2001; 2101-2112.
Schmitt, T.M., et al.; "Induction of T Cell Development from Hematopoietic Progenitor Cells by Delta-like-1 In Vitro"; Immunity; vol. 17; Dec. 2002; 749-756.
Komai-Koma, M., et al.; "Chemoattraction of Human T Cells by IL-18"; J Immunol; vol. 170; 2003; 1084-1090.
Gracie, J.A., et al.; "Interleukin-18"; Journal of Leukocyte Biology; vol. 73, No. 2; Feb. 2003; 213-224.
Broers, A.E.C., et al.; "Interleukin-7 improves T-cell recovery after experimental T-cell-depleted bone marrow transplantation in T-cell-deficient mice by strong expansion of recent thymic emigrants"; Blood; vol. 102, No. 4; Aug. 15, 2003; 1534-1540.
Finotto, S., et al.; "Severe hepatic injury in interleukin 18 (IL-18) transgenic mice: a key role for IL-18 in regulating hepatocyte apoptosis in vivo"; Gut; vol. 53; 2004; 392-400.

(Continued)

*Primary Examiner* — Bridget E Bunner
*Assistant Examiner* — Fozia Hamud
(74) *Attorney, Agent, or Firm* — Hall Estill Law Firm

(57) ABSTRACT

Therapies using IL-18 alone or in combination with IL-7 for rebuilding weakened immune systems by increasing progenitor cell yields from bone marrow stem cells and/or increasing stem cell engraftment in bone marrow.

3 Claims, 8 Drawing Sheets

(56) References Cited

PUBLICATIONS

Wren, J.D., et al.; "Knowledge discovery by automated identification and ranking of implicit relationships"; Bioinformatics; vol. 20, No. 3; 2004; 389-398.

Wren, J.D., et al.; "Shared relationship analysis: ranking set cohesion and commonalities within a literature-derived relationship network"; Bioinformatics; vol. 20, No. 2; 2004; 191-198.

Chu, Y., et al.; "Exogenous IL-7 increases recent thymic emigrants in peripheral lymphoid tissue without enhanced thymic function"; Blood; Aug. 15, 2004; vol. 104, No. 4; 1110-1020.

Wren, J.D.; "Extending the mutual information measure to rank inferred literature relationships"; BMC Bioinformatics; vol. 5; Oct. 7, 2004; 13 pages.

Rodriguez-Galan, M.C., et al.; "Synergistic Effect of IL-2, IL-12, and IL-18 on Thymoctye Apoptosis and Th1/Th2 Cytokine Expression"; J Immunol; vol. 174; 2005; 2796-2804.

Huang, J., et al.; "Propensity of Adult Lymphoid Progenitors to Progress to DN2/3 Stage Thymocytes with Notch Receptor Ligation"; J Immunol; vol. 175, No. 8; Oct. 15, 2008; 4858-4865.

Massa, S., et al.; "Critical role for c-kit (CD117) in T cell lineage commitment and early thymocyte development in vitro"; Eur. J. Immunol.; vol. 36; 2006; 526-532.

Sasson, S.C., et al.; "The IL-7IL-7 Receptor Axis: Understanding its Central Role in T-Cell Homeostatis and the Challenges Facing its Utilization as a Novel Therapy"; Current Drug Targets; vol. 7; 2006; 1571-1582.

Ito, H., et al.; "IL-18 produced by thymic epithelial cells induces development of dendritic cells with CD11b in the fetal thymus"; International Immunology; vol. 18, No. 8; 1253-1263, Jun. 2006.

Gutcher, I., et al.; "Interleukin 18-independent engagement of interleukin 18 receptor-x is required for autoimmune inflammation"; Nature Immunology; vol. 7, No. 9; Sep. 2006; 946-953.

Vandewiele, C.J., et al.; "Impaired thymopoiesis in interleukin-7 receptor transgenic mice is not corrected by Bcl-2"; Cellular Immunology; vol. 250; 2007; 31-39.

Jahn, T., et al.; "Direct interaction between Kit and the interleukin-7 receptor"; Blood; vol. 110, No. 6; Sep. 15, 2007; 1840-1848.

Goldberg, G.L., et al.; "Clinical Strategies to Enhance T cell Reconstitution"; Semin Immunol.; vol. 19, No. 5; Oct. 2007; 289-296.

Arend, W.P., et al.; "IL-1, IL-18, and IL-33 families of cytokines"; Immunological Reviews; vol. 223, No. 1; 2008; 20-38.

Iwai, Y., et al.; "An IFN-y-IL-18 Signaling Loop Accelerates Memory CF8+ T Cell Proliferation"; Plos One; vol. 3, No. 6; Jun. 2008; 9 pages.

Gruver, A.L., et al.; "Cytokines, leptin, and stress-induced thymic atrophy"; J Leukoc Biol.; vol. 84, No. 4; Oct. 2008; 915-923.

Wren, J.D.; "A global meta-analysis of microarray expression data to predict unknown gene functions and estimate the literature-data divide"; Bioinformatics; vol. 25, No. 13; 2009; 1694-1701.

Holmes, R., et al.; "The OP9-DL1 System: Generation of T-Lymphocytes from Embryonic or Hematopoietic Stem Cells In Vitro"; Cold Spring Harbor Protocol; vol. 4, No. 2; Feb. 2009; 1-13.

Tarhini, A.A., et al.; "A Phase 2, Randomized Study of SB-485232, rhIL-18, in Patients With Previously Untreated Metastatic Melanoma"; Cancer; Feb. 15, 2009; 859-868.

Capitini, C.M., et al.; "Modulating T cell Homeostasis with IL-7: Preclinical and Clinical Studies"; J Intern Med.; vol. 266, No. 2; Aug. 2009; 141-153.

Daum, J.R., et al.; "Ska3 Is Required for Spindle Checkpoint Silencing and the Maintenance of Chromosome Cohesion in Mitosis"; Current Biology; vol. 19; Sep. 15, 2009; 1467-1472.

Srivastava, S., et al.; "Interleukin-18: Biology and Role in the Immunotherapy of Cancer"; Current Medicinal Chemistry; vol. 17; 2010; 3353-3357.

Tan, C., et al.; "Ten-Color flow cytometry reveals distinct patterns of expression of CD124 and CDE126 by developing thymocytes"; BMC Immunology; vol. 12, No. 36; 2011; 9 pages.

Billard, M.J., et al.; "Acute Endotoxin-Induced Thymic Atrophy Is Characterized By Intrthymic Inflammatory and Wound Healing Responses"; Plos One; vol. 6, No. 3; Mar. 2011; 14 pages.

Lupu, C., et al.; "Novel protein ADTRO regulates TFPI expression and function in human endothelial cells in normal conditions and in response to androgen"; Blood; vol. 118, No. 16; Oct. 20, 2011; 4463-4473.

"Notch Regulation of the Immune System"; RADTKE (editor); Springer Heidelberg; 2012; 192 pages.

Youm, Y., et al.; "The NLRP3 Inflammasome Promotes Age-Related Thymic Demise and Immunosenescence"; Cell Reports; vol. 1; Jan. 26, 2012; 56-68.

Clemmensen, S.N., et al.; "Olfactomedin 4 defines a subset of human neutrophils"; J Leukoc Biol.; vol. 91, No. 3; Mar. 2012; 495-500.

Moore, A.J., et al.; "Transcriptional priming of intrathymic precursors for dendritic cell development" Development; vol. 140; 2013; 13 pages.

Zhou, J., et al.; "Interleukin-18 augments growth ability of primary human malanocytes by PTEN inactivation through the AKT/NF=kB pathway"; Internat'l Jour. of Biochem. & Cell Bio.; vol. 45; 2013; 308-316.

Towner, R.A., et al.; "ELTD1, a Potential New Biomarker for Gliomas"; Neurosurgery; vol. 72, No. 1; Jan. 2013; 77-91.

Bourdeau, A., et al.; "Inhibition of T Cell Protein Tyrosine Phosphatase Enhances Interleukin-18-Dependent Hematopoietic Stem Cell Expansion"; Stem Cells; vol. 31; Feb. 2013; 293-304.

Simpkins, F., et al.; "Chemoimmunotherapy Using Pegylated Liposomal Doxorubicin and Interleukin-18 in Recurrent Ovarian Cancer: A Phase I Dose-Escalation Study"; Cancer Immunol Res; vol. 1, No. 3; Sep. 2013; 168-179.

Dinarello, C.A., et al.; "Interleukin-18 and IL-18 binding protein"; Frontiers in Immunology; vol. 4, Art. 289; Oct. 2013; 10 pages.

Towner, R.A., et al.; "Experimental validation of 5 in-silico predicted glioma biomarkers"; Neuro-Oncology; vol. 15, No. 12; Oct. 24, 2013; 1625-1634.

Walsh, M.C., et al,; "IL-18 Synergizes with IL-7 to Drive Slow Proliferation of Naive CD8 T Cells by Costimulating Self-Peptide-Mediated TCR Signals"; J Immunol; vol. 193; 2014 (prepublished online Sep. 8, 2014); 3992-4001.

Kapucu, S., et al.; "Physiological problems in patients undergoing autologous and allogeneic hematopoietic stem cell transplantation"; Asia-Pacific Journal of Oncology Nursing; vol. 1, No. 1; Apr.-Jun. 2014; 5 pages.

"Stem Cell Transplant for Cancer"; American Cancer Society; 2016; 32 pages.

* cited by examiner

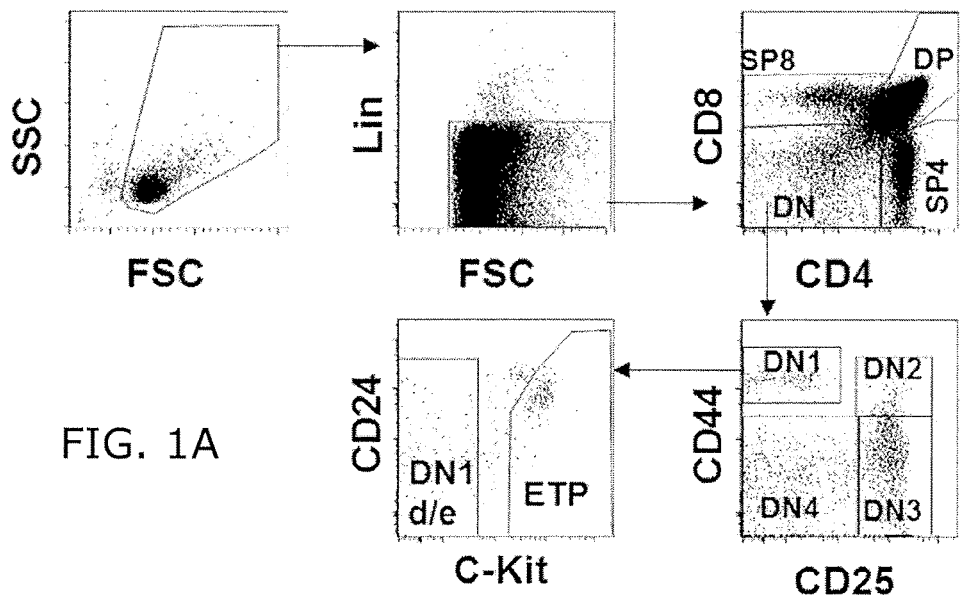
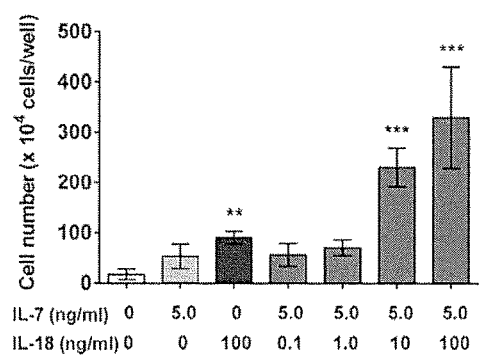
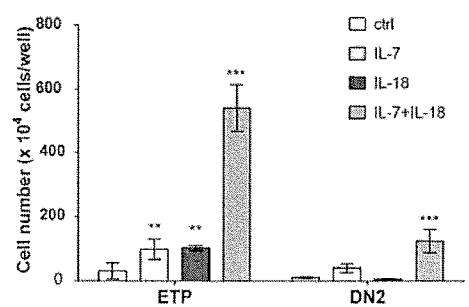
FIG. 1A
FIG. 1B
FIG. 1C

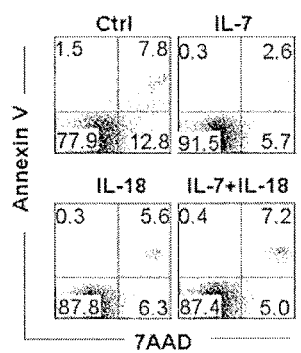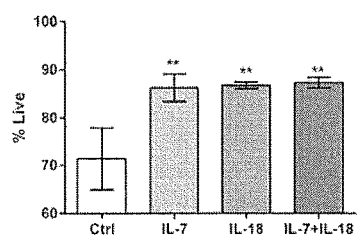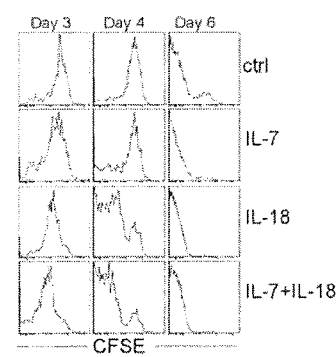
FIG. 2A  FIG. 2B

FIG. 3A
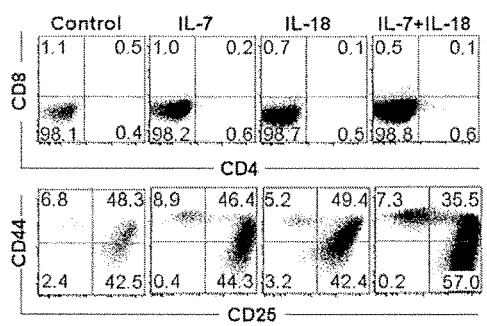
FIG. 3B
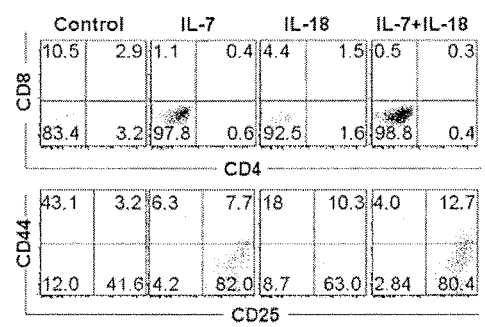
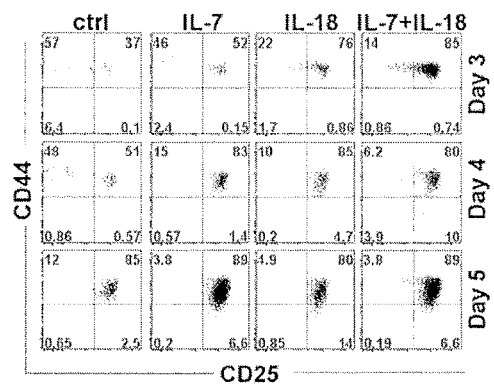
FIG. 3C
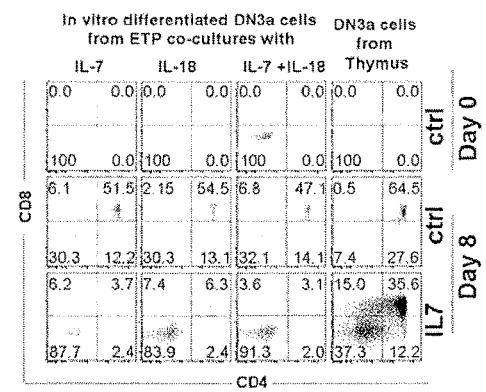
FIG. 3D

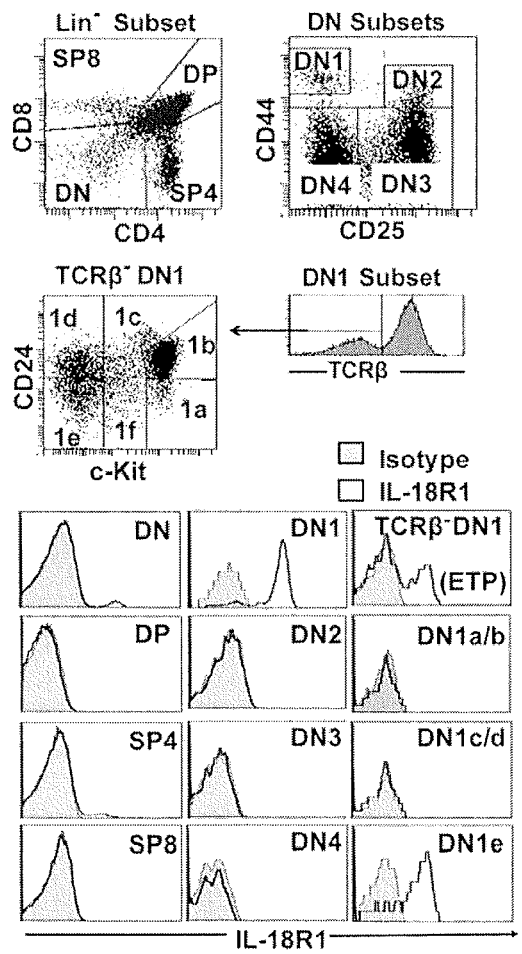
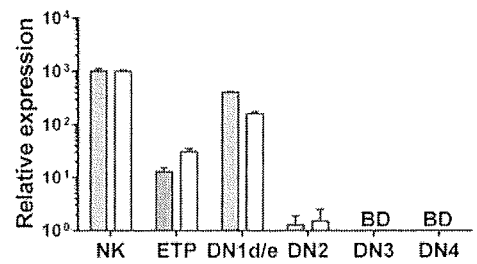
FIG. 4B
FIG. 4A

FIG. 6A
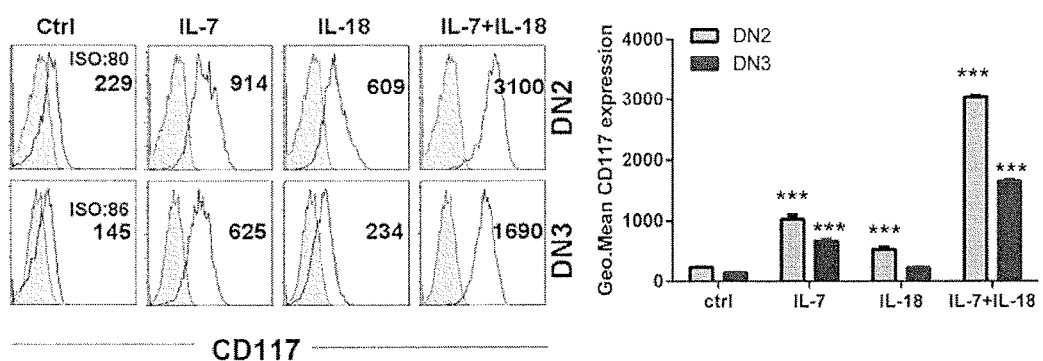
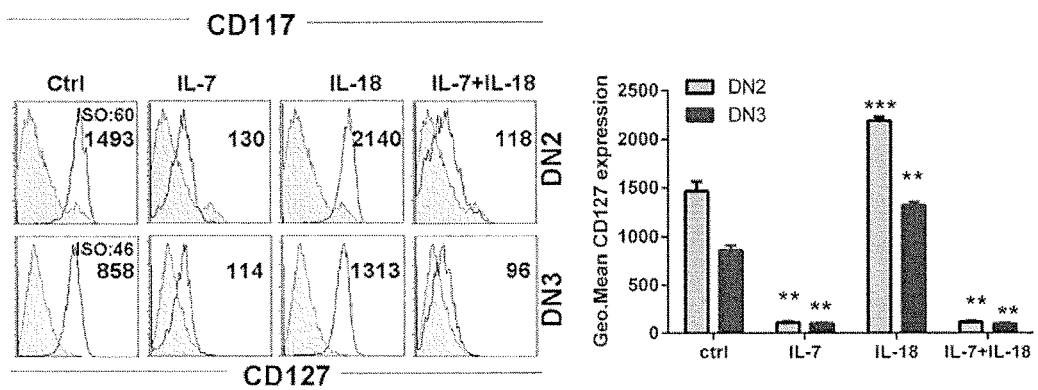
FIG. 6B

ENHANCING PROGENITOR CELL NUMBERS

CROSS-REFERENCE TO RELATED APPLICATIONS

This application claims priority and benefit of U.S. Provisional Application Ser. No. 62/082,816, filed Nov. 21, 2014, the entirety of which is hereby expressly incorporated herein by reference.

GOVERNMENT SUPPORT

The present work has been supported by NIH grants GM103636, RR020143-07 and GM103456. The U.S. government has certain rights in this invention.

BACKGROUND

IL (Interleukin)-18 was originally described as IFN-γ-inducing factor because it was able to augment the production of IFN-γ from T cells and NK cells. As part of the IL-1 cytokine family, IL-18 is a multi-functional component of both the innate and the acquired immune response. Under various conditions the IL-18R1 and IL-18RAP (IL-18 Receptor Accessory Protein) are expressed on a variety of immune cells including NK cells, macrophages, neutrophils, B cells, and fully differentiated Th1 cells. IL-18 has been shown to work in synergy with other cytokines, including IL-12 and IL-4 and has been broadly implicated in autoimmune and inflammatory diseases as well as chronic allergic rhinitis and asthma. In the periphery, IL-18 is known to exert an influence on numerous and diverse T cell processes. It increases Fas ligand-mediated cytotoxicity on T cells and stimulates the development of CD8 effector T cells. IL-18 also promotes chemotaxis of T cells. Furthermore, IL-18 drives CD4 T cell effector responses; inducing IFN-γ production by Th1 cells and promoting production of IL-4, IL-5 and IL-13 in Th2 cells. IL-18 can also enhance Th2 responses (with IL-2) and is indispensable for Th17 responses. Transgenic overexpression of IL-18 h ad dramatic effects on the immune system, however, these studies did not focus on the effects on early thymocytes, perhaps due to the important role for this cytokine in Th1 and Th2 differentiation that has kept the spotlight on peripheral immune cell mechanisms. Although the immunomodulatory functions of IL-18 are relatively well defined, its potential role in hematopoiesis has not been investigated. Previous studies have demonstrated thymic expression of IL-18 and this cytokine has been shown to promote the differentiation of fetal DN thymocytes to thymic-derived dendritic cells. Furthermore, thymocyte stimulation with IL-18 can elicit production of Th1 and Th2 cytokines in the presence of IL-12 and IL-2, respectively.

BRIEF DESCRIPTION OF THE DRAWINGS

The appended drawings illustrate several embodiments of the present disclosure. It is to be noted however, that the appended drawings only illustrate several typical embodiments and are therefore not intended to be considered limiting of the scope of the present disclosure.

FIGS. 1A-1C show enhanced ETP and DN2 thymocyte expansion in the presence of IL-18. A) Gating strategy used for discriminating ETP and DN2 thymocyte subsets. Sort-purified ETP or DN2 thymocytes were co-cultured on OP9-DL4 stromal cells in culture media supplemented with IL-18 or IL-7 alone or in combination and cell yields on day 7 were measured using a hemocytometer. B) Cell number in ETP cultures stimulated with indicated concentrations of IL-7 and IL-18. C) Cell yields in ETP and DN2 cultures stimulated with 5 ng/ml IL-7 and 100 ng/ml IL-18. Data are presented as mean±SEM of 3 replicate wells for each experimental condition and are representative of three experiments with similar results. *$p<0.001$, $p<0.05$.

FIGS. 2A-2B show enhanced proliferation and survival of ETP in the presence of IL-7 and IL-18. Sort-purified ETPs were co-cultured with OP9-DL4 stromal cells in media supplemented with IL-18 or IL-7 alone or in combination. A) Survival of cells after 7 days of culture was assessed using Annexin V and 7AAD binding (percentages of cells in each quadrant are represented as the mean±SEM of 3 replicates wells). B) CSFE dilution profiles for ETPs expanding under indicated conditions on day 3, 4, or 6. Histograms are representative of duplicate samples from each experimental condition and are representative of at least three experiments with similar results. **$p<0.05$ FIGS. 3A-3D show that IL-7 and IL-18 accelerate ETP differentiation without skewing to a particular subset. Sort purified ETP or DN2 thymocytes were co-cultured with OP9-DL4 stromal cells in media supplemented with IL-18 or IL-7 alone or in combination. Differentiation of ETP and DN2 cells into more mature thymocytes were assessed by discriminating cells in the cultures using standard phenotypic markers. Thymocyte subsets identified in ETP/OP9-DL4 (A) or DN2/OP9-DL4 (B) co-cultures on day 7 under indicated conditions are shown. C) Thymocyte subsets identified in ETP/OP9-DL4 co-cultures during five-day expansion of ETPs under indicated conditions. D) DN3a thymocytes sorted from day 7 ETP or DN2 co-cultures or thymus from C57BL/6 mouse were further cultured for 7 days on OP9-DL4 stromal cells and their differentiation into SP4, SP8 or DP cells were analyzed using phenotypic markers. Dot plots were representative of 2-3 replicates in each treatment and each experiment was repeated at least three times with similar results.

FIGS. 4A-4B demonstrate the IL-18 receptor is differentially expressed on thymocyte subsets. A) IL-18R1 protein expression evaluated by flow cytometry on freshly isolated thymocytes from C57BL/6 mouse. B) Real-time RT-PCR assessment of IL-18R1 (grey bar) and IL-18RAP (white bar) transcript abundance relative to GAPDH in sort-purified thymocyte subsets and NK cells from spleen. Data are representative of experiments repeated at least twice with similar results.

FIGS. 6A-6B show IL-18 induced upregulation of c-kit and IL-7 Rα surface expression on ETP-OP9DL4 co-cultures. Sort purified ETPs from C57BL/6 mouse thymocytes were co-cultured for 7 days with OP9-DL4 stromal cells supplemented with IL-18 or IL-7 alone or in combination. DN2 and DN3 cell surface of (A) c-Kit (CD117) and (B) IL-7R☐ (CD127) was analyzed by flow cytometry. Histograms are representative of three replicates in each treatment. Numbers in the histograms represent geometrical mean fluorescence intensity of CD117 or CD127 or their respective isotype control (ISO) staining. Bars represent mean±SEM of receptor expression, as determined by fluorescence intensity, from 3 replicate wells in each treatment. Data here are representative of three experiments with similar results. ***$p<0.001$.

DETAILED DESCRIPTION

Figure 5:
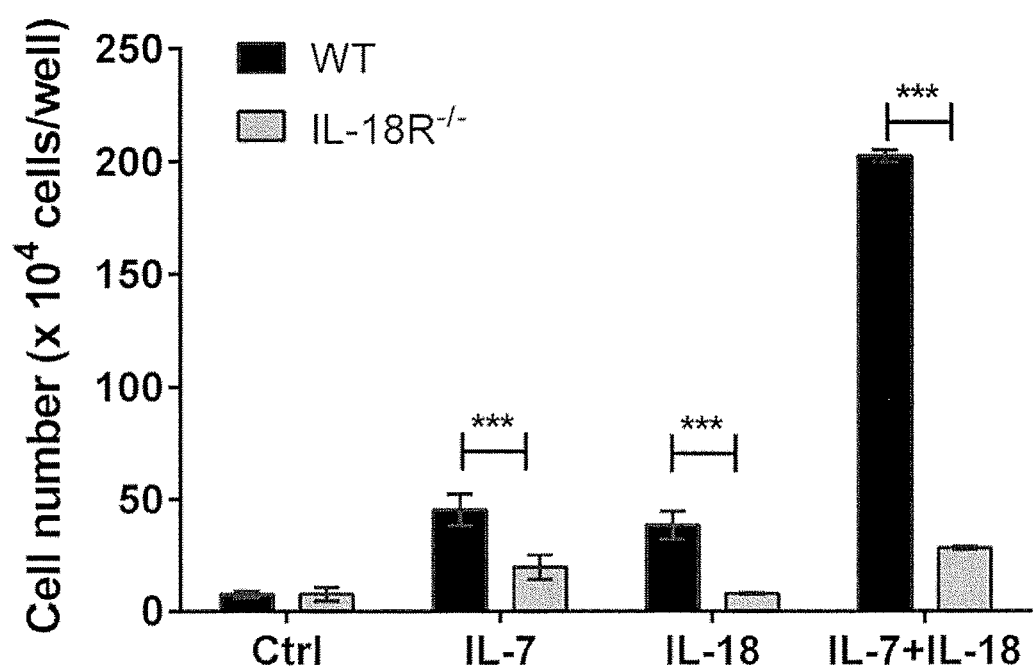
FIG. 5 shows IL-18 induced increase in ETP expansion requires IL-18 receptor expression. Sort purified ETPs from wildtype or IL-18R1$^{-/-}$ mouse thymocytes were co-cultured with OP9-DL4 stromal cells in media supplemented with IL-18 or IL-7 alone or in combination and cell yields from day 7 co-cultures were measured using a hemocytometer. Data are presented as means±SEM of three replicates wells from each experimental condition and are representative of three experiments with similar results. ***$p<0.001$.

The present disclosure is directed to novel therapies using IL-18 alone or in combination with IL-7 for rebuilding weakened immune systems by increasing cell yields from bone marrow stem cells and/or increasing stem cell engraftment in bone marrow. The novel therapies can be used, for example, to treat patients who are leukopenic or lymphopenic to boost their white blood cell counts, can be used to treat bone marrow cells taken from patients to grow these cells in vitro for subsequent re-introduction into the body, and/or can be used to enhance numbers of successfully engrafted hematopoietic stem cells after engraftment procedures.

Before further describing various embodiments of the compositions and methods of the present disclosure in more detail by way of exemplary description, examples, and results, it is to be understood that the methods and compositions of present disclosure are not limited in application to the details of specific embodiments and examples as set forth in the following description. The description provided herein is intended for purposes of illustration only and is not intended to be construed in a limiting sense. As such, the language used herein is intended to be given the broadest possible scope and meaning; and the embodiments and examples are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the present disclosure. However, it will be apparent to a person having ordinary skill in the art that the present disclosure may be practiced without these specific details. In other instances, features which are well known to persons of ordinary skill in the art have not been described in detail to avoid unnecessary complication of the description. It is intended that all alternatives, substitutions, modifications and equivalents apparent to those having ordinary skill in the art are included within the scope of the present disclosure. All of the compositions and methods of production and application and use thereof disclosed herein can be made and executed without undue experimentation in light of the present disclosure. Thus, while the compositions and methods of the present disclosure have been described in terms of particular embodiments, it will be apparent to those of skill in the art that variations may be applied to the compositions and/or methods and in the steps or in the sequence of steps of the methods described herein without departing from the concept, spirit, and scope of the inventive concepts.

All patents, published patent applications, and non-patent publications mentioned in the specification are indicative of the level of skill of those skilled in the art to which the present disclosure pertains. U.S. Provisional patent application Ser. No. 62/082,816 filed on Nov. 21, 2014, and all patents, published patent applications, and non-patent publications referenced in any portion of this application are herein expressly incorporated by reference in their entirety to the same extent as if each individual patent or publication was specifically and individually indicated to be incorporated by reference.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism without reference to how the active agent has its physiological effects.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species (e.g., the peptide compound) is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

The terms "subject" and "patient" are used interchangeably herein and will be understood to refer to a warm blooded animal, particularly a mammal. Non-limiting examples of animals within the scope and meaning of this term include dogs, cats, rats, mice, guinea pigs, chinchillas, horses, goats, cattle, sheep, zoo animals, Old and New World monkeys, non-human primates, and humans.

"Treatment" refers to therapeutic treatments. "Prevention" refers to prophylactic or preventative treatment measures. The term "treating" refers to administering the composition to a patient for therapeutic purposes and/or for prevention.

The terms "therapeutic composition" and "pharmaceutical composition" refer to an active agent-containing composition (e.g., IL-18 and/or IL-7) that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of an active agent which is sufficient to exhibit a detectable therapeutic effect in a subject without excessive adverse side effects (such as toxicity, irritation and allergic response) commensurate with a reasonable benefit/risk ratio when used in the manner of the present disclosure. The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "expansion" where used herein refers to an increase in numbers or quantity of for example, progenitor cells.

The terms IL-18 and IL-7 where used herein are intended to include all mutants and variants of wild type IL-18 and IL-7 that have activity similar to wild type IL-18 and IL-7.

Certain embodiments of the present disclosure include a kit comprising (a) a container that contains one or more components or pharmaceutical compositions as described herein (e.g., comprising IL-18 and/or IL-7), in solution or in lyophilized form; (b) optionally, a second container containing a diluent or reconstituting solution for the lyophilized formulation; and (c) optionally, instructions for (i) use of the solution or (ii) reconstitution and/or use of the lyophilized formulation. The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The container may be formed from a variety of materials such as glass or plastic. The kit and/or container may contains instructions on or associated with the container that indicates directions for reconstitution and/or use. For example, the label may indicate that the lyophilized formulation is to be reconstituted to protein concentrations or dosages as described elsewhere herein. The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution). The kit may further include other materials desirable from a commercial and user standpoint, including other buffers, diluents, filters, needles, syringes, and package inserts with instructions for use.

Abbreviations used herein include: CLPs—common lymphoid progenitors; CFSE—carboxyfluorescein succinimidyl ester; DL—Delta-like; DN—Double Negative; DN1—double negative 1; DN2—double negative 2; DN3—double negative 3; DN4—double negative 4; DP—Double Positive Thymocyte; ETPs—Early Thymic Progenitors (also known as "early T lineage progenitors" and "early thymocyte progenitors"); HSCs—hematopoietic stem cells; IL-18—Interleukin-18; IL-7—Interleukin-7; IL18RAP—IL18 Receptor Accessory Protein; IL18r1—IL-18 receptor 1; IL-7Rα—IL-7 receptor subunit alpha; ISP—Immature Single Positive; SP—Single Positive Thymocyte; SP4—single positive 4; SP8—single positive 8.

As noted above, IL-18 is a member of the IL-1 cytokine family that has been extensively characterized as a mediator of inflammatory immune responses. However, IL-18 has not previously been shown to promote hematopoiesis. To assess a potential role for IL-18 in T lymphopoiesis, we sort-purified mouse bone marrow progenitors such as CLPs, HSCs, ETPs and DN2 thymocytes and cultured these populations on OP9-DL4 stromal layers in the presence or absence of IL-18 and/or IL-7. After one week of culture, IL-18 promoted proliferation and accelerated differentiation of ETPs to the DN3 stage, similar in efficiency to IL-7. Furthermore, IL-18 acted synergistically with IL-7 and greatly enhanced the proliferation of thymus derived progenitor cells as well as bone marrow derived CLPs (Lin$^-$ c-kit$^+$ CD127$^+$) and HSCs. This synergistic effect correlated with increased surface expression of c-Kit and IL-7 receptors on the IL-18-treated cells.

Materials and Methods

Mice:

C57BL/6 mice were bred and housed at the University of Oklahoma-Tulsa Comparative Medicine satellite facility under the oversight of the University of Oklahoma Health Science Center Comparative Medicine Facility (Oklahoma City, Okla.), an Association for Assessment and Accreditation of Laboratory Animal Care (AAALAC) approved animal facility. Animal husbandry and all experiments were performed in accordance with procedures outlined in the Guide for the Care and Use of Laboratory Animals (National Research Council). Protocols were reviewed and approved by the Institutional Animal Care and Use Committee of the University of Oklahoma Health Science Center. Mice used in this study were females ranging from 6 to 12 weeks of age. IL18r1-deficient mice (Strain B6.129P2-I118r1$^{tm1AK1}$/J) on a C57BL/6 background (26) were purchased from the Jackson Laboratory (Bar Harbor, Me.).

Tissue Harvest and Cell Staining:

Thymuses were harvested and placed into complete tumor media (CTM) as previously described (27). Thymuses were crushed through 70-μm nylon cell strainers to produce single thymocyte suspensions. Cells were treated with RBC lysis buffer (Sigma-Aldrich, St. Louis, Mo.) and washed into CTM prior to counting. At a concentration of 1×10$^8$ cells/ml, thymocytes were incubated with mAb against mouse CD16/CD32 (Fc Block) (BD Biosciences, San Jose, Calif.) to block potential Fc-mediated binding and then stained at a density of 1×10$^8$ cell/ml with primary mAbs for DN3a, DN3b and DN4a sorts: CD4-bio, CD8-bio, TCRγδ-bio, TCR-β-bio, Lin-bio (28), CD25-PE, CD44-APC-Cy7, CD28-FITC for 45 minutes at 4° C. in the dark. After two washes, the cells were further stained with SA-PE Texas Red for 30 minutes at 4° C. in the dark. ISP (CD4$^-$CD8$^+$CD24$^{hi}$TCR-β$^-$) cells were sorted-purified by staining with CD4-APC, CD8-FITC, TCR-β-PE-Cy7, and CD24-PE. ETP and DN2 cells were sorted-purified, as shown in FIG. 1A, by staining with the following fluorochrome and biotin coupled mAbs followed by SA-PE Texas Red: CD4-bio, CD8-bio, TCRγδ-bio, TCR-β-bio Lin-bio (28), CD25-PE, CD44-APC-Cy7, c-kit-FITC. To assess proliferation kinetics, ETPs were labeled with CFSE (Life Technologies, Grand Island, N.Y.) prior to placing in co-culture. CFSE labeling was performed by incubating cells at room temperature for 10 min in PBS solution containing 1% FBS and 5 μM CFSE and removing excess CFSE by washing cells with culture media. 1000 cells from each population were cultured in replicate wells in a 24-well plate containing confluent OP9-DL4 stromal cells with/without cytokine(s). All cytokines were obtained from R&D Systems (Minneapolis, Minn.). Unless otherwise indicated cytokine concentrations were as follows: IL-7 (5 ng/ml), and IL-18 (100 ng/ml).

For isolating HSCs (Lin$^-$Kit$^+$CD127$^-$) and CLPs (Lin$^-$Kit$^+$CD127$^+$) single cell suspensions of bone marrow isolated from WT mice were processed to remove RBC and block potential FC-mediated antibody binding by treating cells with RBC lysis buffer followed by staining with CD16/CD32 antibody. Bone marrow cells (1×10$^8$ cells/ml) were then stained with biotin conjugated lineage cocktail (CD45RA (clone:14.8), Gr1 (clone:RB6-8C5), CD11b (clone: M1/70), Ter119 (clone: TER-119), CD45/B220 (clone: RA3-6B2), CD2 (clone RM2-5), CD3 (clone: 145-2C11), Cd8 (clone: 53.6.7), CD49b (clone: DX5), and CD19 (clone:1D3)), c-kit-APC, and CD127-PE anti-mouse mAb followed by staining with SA-PE Texas Red for sort purifying HSCs and CLPs.

After times indicated in the Results section, the co-cultured cells were harvested by aspirating and discarding half the culture volume then re-suspending the co-cultured cells by forceful pipetting in the remaining culture volume followed by straining through a 30 μm mesh to remove any detached OP9-DL4 monolayer cell aggregates from the plate. Any remaining OP9-DL4 cells were further discriminated from thymocytes by gating using forward and side scatter; gating out the much larger OP9 cells. The cells were stained with CD4-APC, CD8-Pacific Blue, CD25-PE, CD44-APC-Cy7, CD28-FITC, TCR-β-PE-Cy7, TCRγδ-bio, Lin-bio (28), followed by SA-PE Texas Red. To assess changes in IL-18R1, CD117, and CD127 surface expression, cells were stained with FITC-conjugated anti-IL-18R1 (R&D system; clone 112614), APC conjugated anti-CD117 (Biolegend; clone 2B8), or PE conjugated anti-CD127 (eBioscience; clone A7R34) and the geometric mean fluorescence intensity for IL-18R1, CD117, and CD127 staining on gated population was compared with respective isotype control staining intensities.

Flow Cytometry:

Freshly isolated thymocytes were stained as described above to discriminate the DN, DP, SP4, SP8, DN1-4, and the DN3/DN4 subsets (29) to establish gating parameters for cells harvested from OP9-DL4 co-cultures. A MoFlo cell sorter with Summit v4.3 software (Beckman Coulter, Fullerton, Calif.) was used for the experiments that included sorted populations. Cells were analyzed using a BD LSRII 4-laser flow cytometer and FACS Diva (BD Biosciences, San Jose, Calif.) and FlowJo software (Tree Star, Ashland, Oreg.).

OP9-DL4 Co-Cultures:

The OP9-DL4 cell line was kindly provided by Juan Carlos Zúñiga-Pflücker and maintained according to protocols from his laboratory (30). For each experiment a fresh vial was thawed and grown to 60-80% confluence on treated plates; cells were then split and grown again to 60-80% confluence before the final plating on experimental 24-well treated plates. Sorted thymocyte subsets were co-cultured in plates with the OP9-DL4 stromal cells in αMEM (Invitrogen, N.Y.) supplemented with 16.5% FBS (Sigma-Aldrich) and penicillin-streptomycin (Sigma-Aldrich) (culture media) and the cytokines indicated in the figures. It should be noted that no Flt3L was added to any of the cultures. After 7 days, the cells were harvested from the wells, counted, and stained for flow cytometry. Viable cell counts were obtained using 0.4% Trypan Blue (Lonza Inc, Allendale, N.Y.) staining or annexin V and 7AAD staining technique.

Quantitative Real Time RT-PCR:

Total RNA from sort-purified thymocyte subsets ($2 \times 10^4$ cells) and splenic NK cells ($1 \times 10^5$) were isolated using Qiagen (Germantown, Md.) Mini-Elute columns. Total RNA was reverse transcribed to cDNA using a Qiagen Sensiscript Reverse Transcriptase kit. IL-18 receptor transcript abundance was measured by amplifying cDNA using IL-18Rα and IL-18Rβ primers from Quantitect (Qiagen) and quantifying by the SYBR Green detection method using a ViiA™ 7 Real-Time PCR System (Life Technologies).

Human Recombinant IL-7 and IL-18

Recombinant human IL-7 is available under the name CYT107™, manufactured by Cytheris SA. Recombinant human IL-18 is available under the name SB-485232™, manufactured by GlaxoSmithKline.

Data Analysis:

Flow cytometry data was analyzed using FACS Diva (BD Biosciences, San Jose, Calif.) and FlowJo software (Tree Star, Ashland, Oreg.). Statistical analysis was performed using Graphpad Prism 6 Software and statistical significance between variables was estimated by performing One-way ANOVA and Fischer's test for multiple comparisons.

Results

IL-18 Acts in Synergy with IL-7 to Induce Expansion of ETPs on OP9-DL4 Stromal Cells An IL-18 dose-response was performed in order to determine the effect of IL-18 on immature thymocytes in culture. Sort purified ETPs were cultured for one week on OP9-DL4 stroma with IL-7 added at a constant 5 ng/ml in conjunction with IL-18 at concentrations ranging from 0.1 ng/ml to 100 ng/ml. Supplementing co-cultures with IL-18 significantly enhanced the expansion of ETPs, as determined by total cell yields on day 7, compared to control treatments (FIG. 1B). We observed that the magnitude of ETP expansion in the presence of IL-18 alone was comparable to the ETP expansion observed in the presence of IL-7 alone. Adding IL-7 and IL-18 together to the co-cultures greatly increased the cell yields when compared to cultures containing either IL-7 or IL-18 alone. The synergetic effects of IL-18 and IL-7 were evident only at higher doses of IL-18 (≥10 ng/ml). Requirement of a higher IL-18 dose for cell response is not unusual as relatively higher concentrations of IL-18 are known to be required to activate cells in vitro. We next tested whether IL-18 influenced expansion of other immature thymocyte subsets including DN1d/e, DN2, and DN3 populations. We found that neither IL-7 nor IL-18 alone had an apparent effect on the expansion of these thymocytes, although co-cultures supplemented with both IL-7 and IL-18 showed a modest effect in promoting expansion of the DN2 population (FIG. 1C). These results demonstrate that IL-18 can promote expansion of ETPs and can synergize with IL-7 in a dose dependent manner.

IL-7/IL-18 Co-Stimulation Enhances the Proliferation Rate of ETPs in OP9-DL4 Co-Cultures To assess whether increased cell yields in IL-7 and IL-18 stimulated ETP co-cultures were due to enhanced survival or increased proliferation, we measured cell viability in co-cultures by Annexin-V/7AAD staining and monitored cell divisions using a CFSE dilution assay. We observed that the percentage of live cells in ETP co-cultures stimulated with cytokines was significantly higher than that observed in unstimulated co-cultures (FIG. 2A). IL-7 and IL-18 were equally potent in increasing live cell percentages in 7-day co-cultures. There was also no apparent synergistic effect in the IL-7+IL-18 condition, presumably because there was minimal cell death observed in co-cultures stimulated with IL-7 or IL-18 alone. Because the differences in cell survival among the treatments are small, it's unlikely that enhanced ETP expansion in stimulated cultures was entirely due to enhanced survival. Hence, we compared the proliferation kinetics of unstimulated and stimulated ETP co-cultures. CFSE profiles demonstrated that the ETPs had undergone more cell divisions than CFSE staining can reliable detect by day six, irrespective of the culture conditions (FIG. 2B). However, CFSE profiles on day four clearly showed that ETPs stimulated with either IL-7 or IL-18 alone or in combination experienced more divisions compared to unstimulated ETP cultures. Importantly, the synergistic action of IL-7/IL-8 co-administration was observed on day 4. Together, these results support the contention that IL-18 promotes expansion of ETPs by enhancing both survival and proliferation of ETPs.

IL-18 Accelerates the Differentiation of Immature Thymocytes

To determine whether IL-18 could influence the differentiation of immature thymocytes, sort-purified ETPs, DN2s, or DN3s were co-cultured with OP9-DL4 stromal cells in the presence of IL-7 or IL-18 alone or in combination. After 7 days, differentiation of thymocytes in the co-cultures was analyzed by discriminating thymocyte populations using surface markers. Both ETP and DN2 co-cultures supplemented with recombinant IL-7 showed an increase in total cell number after 7 days without any notable changes in the percentages of different thymocyte populations in comparison to untreated co-cultures (FIGS. 3A and 3B). Similarly, ETP and DN2 co-cultures treated with either IL-18 alone or in combination with IL-7 showed an increase in total cell number without skewing the percentages of any particular thymocyte population as compared with IL-7 alone or untreated cultures. However when we evaluated differentiation of ETPs from CFSE dilution assays at earlier time points (FIG. 3C), we saw that the differentiation of ETPs into DN2 and DN3 subsets occurred at a faster rate in IL-7 and IL-18-stimulated cultures compared to unstimulated controls. The CFSE profiles also showed no preferential expansion or differentiation of a particular thymocyte population in co-cultures stimulated in presence of IL18 (data not shown). To determine the capacity for further development along the T cell lineage, we evaluated DN3a thymocyte subsets generated in vitro from ETP/OP9-DL4 co-cultures and fresh ex vivo DN3a thymocytes sort-purified from the thymus for their potential to develop into DP cells. We found that all in vitro generated DN3a subsets, irrespective of the source and treatment conditions, differentiated into DP subsets when co-cultured on OP9-DL4 stromal cells for 7 days (FIG. 3D) in the absence of IL-7. However, in the presence of IL-7 there were significantly fewer DP thymocytes, as evidenced by the percentage of cells within the DP quadrants, from DN3a populations generated from ETP co-cultures as well as from DN3a populations from thymus. This effect is not surprising as IL-7 has been shown to inhibit the transition of DN2/DN3 thymocytes to the DP stage. These results collectively suggest that IL-18 increased the expansion of immature thymocytes without interfering with their differentiation into more mature thymocytes.

ETP and DN2 Subsets Express IL-18 Receptor Transcript but not Discernible Levels of IL-18 Receptor Protein as Assessed by Flow Cytometry To further characterize the mechanism(s) by which IL-18 exerts its effect on developing T cells, surface expression of the IL-18R1 (CD218a) was assessed on the four main thymocyte populations, DN, DP, SP4 and SP8 (FIG. 4A). Only a small percentage of the DN population and the SP4 population stained positively for the IL-18R1. Subdivision of the DN compartment revealed that only the DN1 population contained IL-18R1 expressing cells. Further parsing of the DN1 compartment by CD24 and c-Kit staining showed IL-18R1 surface expression to be restricted to the DN1e population. This is somewhat surprising given that the DN1a/b population (ETPs) expanded in the presence of IL-18 as did both ETPs and DN2 cells with the combination of both IL-7 and IL-18 as shown in FIG. 1C.

Because surface expression of the IL-18R1 was not detectable in the IL-18 responsive ETP and DN2 populations using flow cytometry, we assessed IL-18 receptor expression on ETP, DN1e/d, DN2, and DN3 thymocytes using Real-time RT-PCR. Both ETPs and DN2 expressed low levels of IL-18R1 and IL18Rap mRNA compared to DN1e/d populations and positive control splenic NK cells (FIG. 4B). The OP9-DL4 stromal cells did not express IL-18 receptor either at transcript level or at surface expression (data not shown).

The IL-18 Effect on Thymocyte Expansion is Absent in Cells from IL-18R1 Deficient Mice Although we did not detect surface expression of IL-18 receptors on ETPs or DN2 thymocytes, presence of IL-18 receptor transcripts in these cells suggest the possibility for very low levels of receptor expression. To determine whether the IL-18 effects in the cultures were the direct result of IL-18 receptor engagement we repeated the OP9-DL4 co-cultures described above comparing thymocytes from IL-18R1 null mice to wild type thymocytes. ETPs from either C57/BL6 mice or IL-18R1 null mice (FIG. 5) were plated with no cytokine, IL-7, IL-18, or a combination of IL-7 and IL-18. As expected, the IL-18R1 null mice did not show expansion in response to IL-18. The synergy between IL-18 and IL-7 was also absent in the null mice. This indicated that the IL-18 effects were mediated through the IL-18 receptor even though we were unable to detect IL-18R1 on the surface of the ETPs via flow cytometry.

IL-18-Stimulated ETPs Significantly Upregulate c-Kit and IL-7Rα Receptor Expression To evaluate a potential mechanistic concurrence in our model, we tested the effects of IL-18 on regulation of c-Kit and IL-7Rα expression on immature thymocytes differentiating in the OP9-DL4 co-cultures. ETPs cultured in the presence of IL-7 or IL-18 alone for seven days demonstrated significantly upregulated c-Kit expression on the resulting DN2 and DN3 cells, though the effect was modest in comparison to the effect of adding both cytokines simultaneously (FIG. 6). ETPs exposed to IL-7 plus IL-18 showed robust increases in surface c-Kit expression (~13.5-fold over control), which was significantly greater than what was observed in ETP cultures exposed to IL-7 or IL-18 alone (FIG. 6A). Because IL-18 had a synergistic effect with IL-7, we also assessed the IL-7 receptor expression on these cells when treated with IL-18. As expected, stimulating ETPs with IL-18 caused a significant upregulation of surface IL-7R in differentiating thymocytes after seven days of co-culture (FIG. 6B). ETP cultures exposed to IL-7 with or without IL-18 showed minimal IL-7R expression on the differentiating thymocytes, presumably due to activation-induced receptor internalization.

Figure 7:
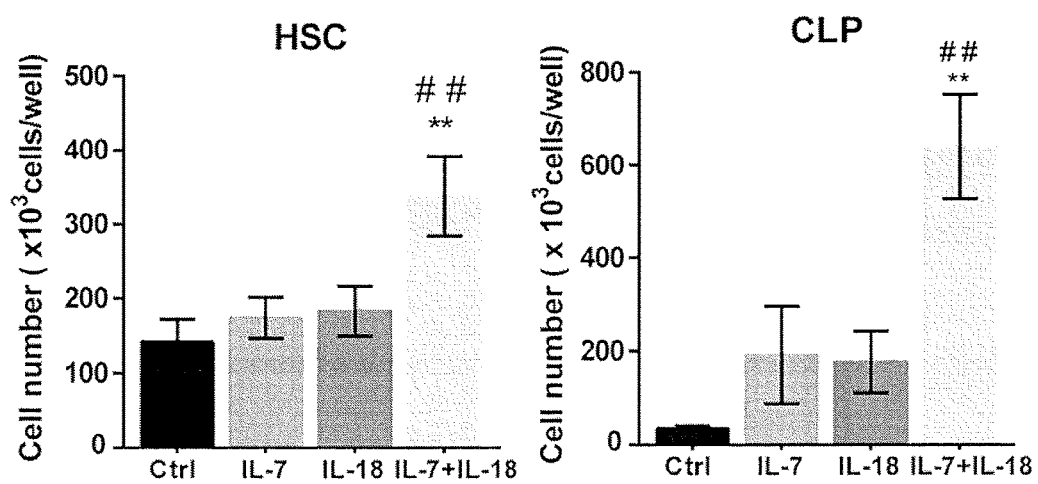
FIG. 7 shows IL-18 promotes expansion of HSCs and CLPs in OP9-DL4 co-cultures. Sort purified HSC ($1\times10^4$ cells) and CLP (500 cells) from C57BL/6 mouse bone marrow were co-cultured with OP9-DL4 stromal cells in media supplemented with IL-18 or IL-7 alone or in combination and cell yields from day 7 co-cultures were measured using a hemocytometer. Data are presented as means±SEM of three replicate wells from each experimental condition and are representative of three experiments with similar results. **Significant with $p<0.05$ compared to controls and ## significant with $p<0.05$ compared to IL-7 or IL-18.

IL-18 Promotes the Expansion of Immature Progenitor Cells in OP9-DL4 Co-Cultures Lack of IL-18-mediated proliferative effects in DN1e/d and DN3 thymocytes despite IL-18 receptor expression in the DN1e/d subset and upregulation of c-kit in response to IL-7 and IL-18 co-stimulation led us to hypothesize that IL-18 proliferative effects are not restricted to immature thymocytes and may be present in other progenitor cells expressing c-kit and IL7 receptors. To test this hypothesis we further investigated the proliferative effects of IL-18 on HSCs and CLPs in the bone marrow, which also express c-kit receptor. We observed that supplementing co-cultures with IL-7 and IL-18 significantly enhanced the proliferation of both HSCs and CLPs co-cultured on the OP9-DL4 stromal cells (FIG. 7), although the proliferative effects of IL-7 and IL-18 combination is modest in co-cultures started with HSCs compared to CLPs.

Combination Treatment of IL-18 and IL-7 Enhances HSC Number In Vivo

Figure 8:
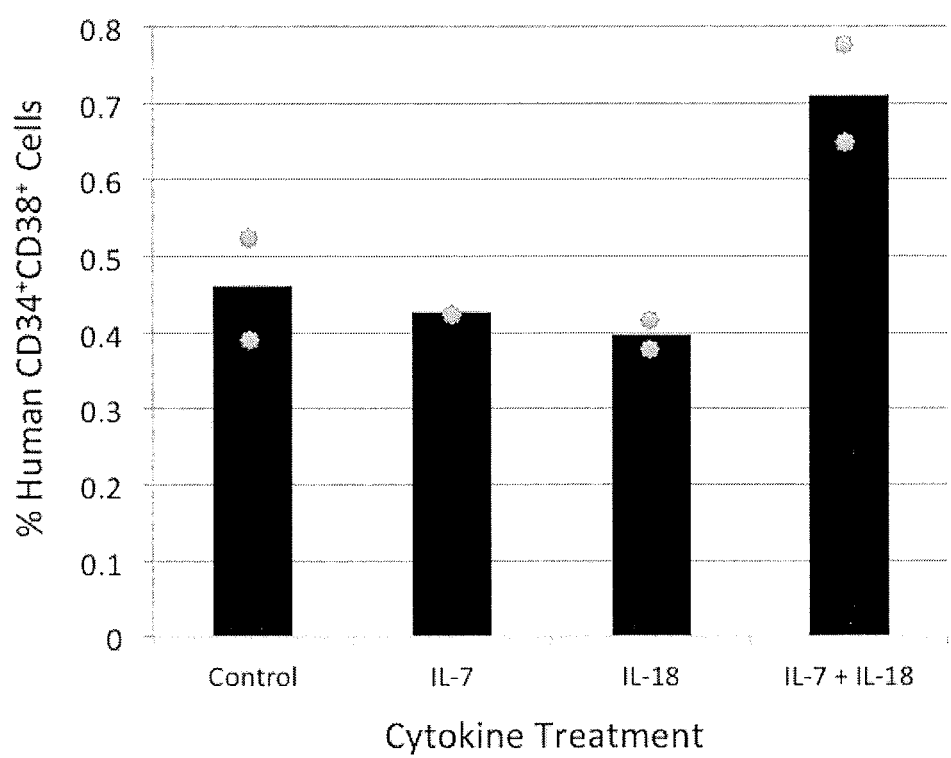
FIG. 8 shows that treatment in vivo with IL-18 in combination with IL-7 boosted human hematopoietic stem numbers in engrafted mice. Bars represent the mean percentages of duplicate mice with the exception of the IL-7 alone treatment, which represents one mouse. Stars represent each individual mouse value.

NOD-Rag1$^{null}$IL-2R$^{null}$ (NRG) mice were injected I.P. with 0.5 mg busulfan in DMSO/RPMI medium to allow for subsequent human stem cell engraftment in the bone marrow. On day 2 after busulfan treatment, each mouse was injected I.V. with 125,000 human bone marrow CD34$^+$ stem cells. On days 3, 6, 9, 12, 15, and 18 mice were injected subcutaneously with 4 μg per mouse recombinant human IL-18 or media control and/or 0.99 μg per mouse I.P. with recombinant human IL-7 or media control. On day 21, mouse bone marrow was harvested and the number of human hematopoietic stem cells was assessed by flow cytometry using monoclonal antibodies specific for human CD34 and CD38. Results are shown in FIG. 8. The experiment demonstrates that a combination treatment of IL-18 and IL-7 enhances the quantity of HSCs engrafted in the bone marrow in vivo. Furthermore, it indicates that an IL-18/IL-7 combination treatment can enhance the quantity of HSC engraftment in human bone marrow as would be predicted from the mouse bone marrow HSC in vitro experiments.

As shown in the results above, IL-18 dramatically influenced T cell development. IL-18 augmented thymocyte proliferation, accelerated differentiation capacity, and in combination with IL-7 enhanced numbers of human HSCs engrafted in bone marrow in vivo. The proliferative effects of IL-18 are not restricted to T cells progenitors but also seen in more immature progenitor cells such as HSC, and CLPs in bone marrow that give raise to all lymphoid derived cells, indicating that IL-18 influences lymphopoiesis in general. While IL-18 has well-established roles in a number of other processes, its involvement in early T cell development has not been well defined.

Proinflammatory cytokines and inflammation in general negatively impact T lymphopoiesis, which is in contrast with the IL-18 effects discovered herein on immature thymocyte bone marrow progenitors. Results presented here clearly demonstrate that under controlled conditions IL-18 can potentiate ETP proliferation and differentiation toward the T-lineage. We have demonstrated herein that IL-18 can substitute for IL-7 in early thymic development processes and acts synergistically with IL-7 in promoting proliferation and engraftment. As demonstrated herein, administration of IL-18 alone, or in combination with IL-7 can be used therapeutically to enhance progenitor cell proliferation and/or engraftment in, for example (but not limited to), patients subjected to organ transplant or chemotherapy who have diminished white blood cell production in the bone marrow. Administration of recombinant IL-7 has been used in clinical trials intended to promote lymphopoiesis under lymphopenic conditions. However, use of IL-7 has limitations such as its bias towards homeostatic expansion of peripheral lymphocytes and its marginal effects on enhancing progenitor cell populations that give rise to lymphocyte diversity. Furthermore, the duration and dose of IL-7 necessary for effect poses a risk of graft versus host disease (GVHD) due to its ability to enhance T cell functions.

Accordingly, the ability of IL-18 to alone, or to act in combination with IL-7 to enhance progenitor cell proliferation and/or engraftment would not be obvious. Based on the robust synergistic effects demonstrated herein for the first time, used together as a combination therapy, IL-18 and IL-7 can overcome the limitations of IL-7 alone. IL-18 enhances the effects of IL-7 on progenitor cells and decreases the dose and duration of IL-7 needed for lymphocyte reconstitution in clinical scenarios of lymphodepletion.

Where used herein, the term "in combination" means that the active agents (e.g., IL-18 and IL-7) can be administered before, after, or at the same time. For example, the quantity of IL-18 can be administered before, after, or at the same time as the quantity of IL-7.

In certain embodiments of the present disclosure, IL-18 alone, or in combination with IL-7, can be used therapeutically in reversing lymphopenic conditions, for example those caused by treatment regimens that cause leukopenia, including but not limited to chemotherapies and irradiation. Additional conditions that result in leukopenia that can be treated by administering IL-18, or IL-18 and IL-7 in combination, include but are not limited to HIV infections and other chronic infections, congenital hematopoietic deficiencies, and toxin exposures. Recombinant human IL-18 can be administered to a subject at a dose ranging, for example, from about 1 µg to about 1000 µg IL-18/kg body weight (e.g., as administrated through subcutaneous, intravenous, or intramuscular injection or other suitable method). In combination with IL-18, recombinant human IL-7 can be administered at a dose ranging, for example, from about 1 µg to about 1000 µg IL-7/kg body weight, together with the IL-18 (e.g., as administrated through subcutaneous or intravenous or intramuscular injection or other suitable method). More particularly, IL-18 may be administered at a dose ranging, for example, from about 25 µg to about 500 µg IL-18/kg body weight. More particularly, IL-18 may be administered at a dose ranging, for example, from about 50 µg to about 300 µg IL-18/kg body weight. More particularly, IL-18 may be administered at a dose ranging, for example, from about 75 µg to about 200 µg IL-18/kg body weight. More particularly, IL-18 may be administered at a dose ranging, for example, from about 100 µg to about 150 µg IL-18/kg body weight. More particularly, IL-7 may be administered at a dose ranging, for example, from about 5 µg to about 500 µg IL-7/kg body weight. More particularly, IL-7 may be administered at a dose ranging, for example, from about 10 µg to about 250 µg IL-7/kg body weight. More particularly, IL-7 may be administered at a dose ranging, for example, from about 20 µg to about 100 µg IL-7/kg body weight. More particularly, IL-7 may be administered at a dose ranging, for example, from about 30 µg to about 75 µg IL-7/kg body weight.

The exact amounts of IL-18 alone, or IL-7 and IL-18 in combination, can be adjusted by the attending physician to obtain optimal therapeutic use with minimal side effects. Existing clinical trials have already demonstrated the safety and efficacy of the IL-7 and IL-18 in humans as therapeutic targets. Based on these data, the combination of IL-7 and IL-18 poses minimal risk and significant benefits by mitigating the limitation of IL-7 used alone as a therapy for treating lymphopenia or for any condition benefiting from enhanced hematopoiesis or enhanced HSC engraftment.

Accordingly, the present disclosure is directed in at least one embodiment to a method of providing a hematopoietic therapy to a subject in need of such therapy, comprising administering an effective amount of an IL-18 to the subject. The hematopoietic therapy may enhance lymphopoiesis in the subject and/or bone marrow engraftment of hematopoietic stem cells and/or survival or proliferation of hematopoietic stem cells administered to the subject. The subject may be undergoing concurrent therapy for a cancer, an infection, and/or an organ transplant. The IL-18 may be administered in combination with IL-7. The present disclosure is also directed in at least one embodiment to a method of enhancing production of hematopoietic progenitor cells, comprising exposing a quantity of bone marrow cells to an effective amount of an IL-18 under conditions suitable for growth of the bone marrow cells. The IL-18 may be administered in combination with IL-7. The present disclosure is also directed in at least one embodiment to a method of providing a hematopoietic therapy to a subject in need of such therapy, comprising injecting the subject with a quantity of CD34+ hematopoietic stem cells, and administering to the subject an amount of IL-18 in combination with an amount of IL-7, whereby the engraftment and/or growth of the hematopoietic stem cells is enhanced. The present disclosure is also directed in at least one embodiment to a method of providing a hematopoietic therapy to a subject in need of such therapy, comprising introducing a quantity of bone marrow cells into the subject, wherein the bone marrow cells were derived from the subject and treated ex vivo with an amount of an IL-18 under conditions suitable for growth and/or differentiation of the bone marrow cells. The IL-18 may be administered to the bone marrow cells in combination with an IL-7. The cell types of these methods that may be enhanced by improved survival, proliferation, or engraftment may include, but are not limited to CLPs (common lymphoid progenitors), DN (double negative) 1, 2, 3, and 4 thymocyte cells, DP (double positive thymocytes), ETPs (early thymic progenitors; HSCs (hematopoietic stem cells at any stage along the development pathway), SP4s (single positive 4 thymocytes), and/or SP8s (single positive 8 thymocytes), B lymphocytes (B cells), natural killer (NK) cells, and NK-T cells.

While the present disclosure has been described in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure. Thus the examples described above, which include particular embodiments, will serve to illustrate the practice of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the presently disclosed methods and compositions. Changes may be made in the formulation of the various compositions described herein, the methods described herein or in the steps or the sequence of steps of the methods described herein without departing from the spirit and scope of the present disclosure.

REFERENCES

1. Wren, J. D. 2009. A global meta-analysis of microarray expression data to predict unknown gene functions and estimate the literature-data divide. *Bioinformatics* 25: 1694-1701.
2. Wren, J. D. 2004. Extending the mutual information measure to rank inferred literature relationships. *BMC bioinformatics* 5: 145.
3. Wren, J. D., R. Bekeredjian, J. A. Stewart, R. V. Shohet, and H. R. Garner. 2004. Knowledge discovery by automated identification and ranking of implicit relationships. *Bioinformatics* 20: 389-398.
4. Wren, J. D., and H. R. Garner. 2004. Shared relationship analysis: ranking set cohesion and commonalities within a literature-derived relationship network. *Bioinformatics* 20: 191-198.
5. Daum, J. R., J. D. Wren, J. J. Daniel, S. Sivakumar, J. N. McAvoy, T. A. Potapova, and G. J. Gorbsky. 2009. Ska3 is required for spindle checkpoint silencing and the maintenance of chromosome cohesion in mitosis. *Current biology: CB* 19: 1467-1472.
6. Towner, R. A., R. L. Jensen, H. Colman, B. Vaillant, N. Smith, R. Casteel, D. Saunders, D. L. Gillespie, R. Silasi-Mansat, F. Lupu, C. B. Giles, and J. D. Wren. 2013. ELTD1, a potential new biomarker for gliomas. *Neurosurgery* 72: 77-90; discussion 91.
7. Clemmensen, S. N., C. T. Bohr, S. Rorvig, A. Glenthoj, H. Mora-Jensen, E. P. Cramer, L. C. Jacobsen, M. T. Larsen, J. B. Cowland, J. T. Tanassi, N. H. Heegaard, J. D. Wren, A. N. Silahtaroglu, and N. Borregaard. 2012. Olfactomedin 4 defines a subset of human neutrophils. *Journal of leukocyte biology* 91: 495-500.
8. Lupu, C., H. Zhu, N. I. Popescu, J. D. Wren, and F. Lupu. 2011. Novel protein ADTRP regulates TFPI expression and function in human endothelial cells in normal conditions and in response to androgen. *Blood* 118: 4463-4471.
9. Towner, R. A., R. L. Jensen, B. Vaillant, H. Colman, D. Saunders, C. B. Giles, and J. D. Wren. 2013. Experimental validation of 5 in-silico predicted glioma biomarkers. *Neuro-oncology* 15: 1625-1634.
10. Okamura, H., H. Tsutsi, T. Komatsu, M. Yutsudo, A. Hakura, T. Tanimoto, K. Torigoe, T. Okura, Y. Nukada, K. Hattori, and et al. 1995. Cloning of a new cytokine that induces IFN-gamma production by T cells. *Nature* 378: 88-91.
11. Gracie, J. A., S. E. Robertson, and I. B. McInnes. 2003. Interleukin-18. *Journal of leukocyte biology* 73: 213-224.
12. Arend, W. P., G. Palmer, and C. Gabay. 2008. IL-1, IL-18, and IL-33 families of cytokines. *Immunological reviews* 223: 20-38.
13. Dao, T., K. Ohashi, T. Kayano, M. Kurimoto, and H. Okamura. 1996. Interferon-gamma-inducing factor, a novel cytokine, enhances Fas ligand-mediated cytotoxicity of murine T helper 1 cells. *Cellular immunology* 173: 230-235.
14. Okamoto, I., K. Kohno, T. Tanimoto, H. Ikegami, and M. Kurimoto. 1999. Development of CD8+ effector T cells is differentially regulated by IL-18 and IL-12. *Journal of immunology* 162: 3202-3211.
15. Komai-Koma, M., J. A. Gracie, X. Q. Wei, D. Xu, N. Thomson, I. B. McInnes, and F. Y. Liew. 2003. Chemoattraction of human T cells by IL-18. *Journal of immunology* 170: 1084-1090.
16. Hoshino, T., R. T. Winkler-Pickett, A. T. Mason, J. R. Ortaldo, and H. A. Young. 1999. IL-13 production by NK cells: IL-13-producing NK and T cells are present in vivo in the absence of IFN-gamma. *Journal of immunology* 162: 51-59.
17. Nakanishi, K., T. Yoshimoto, H. Tsutsui, and H. Okamura. 2001. Interleukin-18 is a unique cytokine that stimulates both Th1 and Th2 responses depending on its cytokine milieu. *Cytokine & growth factor reviews* 12: 53-72.
18. Yoshimoto, T., H. Mizutani, H. Tsutsui, N. Noben-Trauth, K. Yamanaka, M. Tanaka, S. Izumi, H. Okamura, W. E. Paul, and K. Nakanishi. 2000. IL-18 induction of IgE: dependence on CD4+ T cells, IL-4 and STAT6. *Nature immunology* 1: 132-137.
19. Gutcher, I., E. Urich, K. Wolter, M. Prinz, and B. Becher. 2006. Interleukin 18-independent engagement of interleukin 18 receptor-alpha is required for autoimmune inflammation. *Nature immunology* 7: 946-953.
20. Finotto, S., J. Siebler, M. Hausding, M. Schipp, S. Wirtz, S. Klein, M. Protschka, A. Doganci, H. A. Lehr, C. Trautwein, R. Khosravi-Far, D. Strand, A. Lohse, P. R. Galle, M. Blessing, and M. F. Neurath. 2004. Severe hepatic injury in interleukin 18 (IL-18) transgenic mice: a key role for IL-18 in regulating hepatocyte apoptosis in vivo. *Gut* 53: 392-400.
21. Hoshino, T., Y. Kawase, M. Okamoto, K. Yokota, K. Yoshino, K. Yamamura, J. Miyazaki, H. A. Young, and K. Oizumi. 2001. Cutting edge: IL-18-transgenic mice: in vivo evidence of a broad role for IL-18 in modulating immune function. *Journal of immunology* 166: 7014-7018.
22. Ito, H., E. Esashi, T. Akiyama, J. Inoue, and A. Miyajima. 2006. IL-18 produced by thymic epithelial cells induces development of dendritic cells with CD11b in the fetal thymus. *International immunology* 18: 1253-1263.
23. Youm, Y. H., T. D. Kanneganti, B. Vandanmagsar, X. Zhu, A. Ravussin, A. Adijiang, J. S. Owen, M. J. Thomas, J. Francis, J. S. Parks, and V. D. Dixit. 2012. The Nlrp3 inflammasome promotes age-related thymic demise and immunosenescence. *Cell reports* 1: 56-68.
24. Rodriguez-Galan, M. C., J. H. Bream, A. Farr, and H. A. Young. 2005. Synergistic effect of IL-2, IL-12, and IL-18 on thymocyte apoptosis and Th1/Th2 cytokine expression. *Journal of immunology* 174: 2796-2804.
25. Holmes, R., and J. C. Zuniga-Pflucker. 2009. The OP9-DL1 system: generation of T-lymphocytes from embryonic or hematopoietic stem cells in vitro. *Cold Spring Harbor protocols* 2009: pdb prot5156.
26. Hoshino, K., H. Tsutsui, T. Kawai, K. Takeda, K. Nakanishi, Y. Takeda, and S. Akira. 1999. Cutting edge: generation of IL-18 receptor-deficient mice: evidence for IL-1 receptor-related protein as an essential IL-18 binding receptor. *Journal of immunology* 162: 5041-5044.
27. Teague, T. K., B. C. Schaefer, D. Hildeman, J. Bender, T. Mitchell, J. W. Kappler, and P. Marrack. 2000. Activation-induced inhibition of interleukin 6-mediated T cell survival and signal transducer and activator of transcription 1 signaling. *The Journal of experimental medicine* 191: 915-926.
28. Van de Wiele, C. J., J. H. Marino, C. Tan, H. A. Kneale, J. Weber, J. N. Morelli, B. K. Davis, A. A. Taylor, and T. K. Teague. 2007. Impaired thymopoiesis in interleukin-7 receptor transgenic mice is not corrected by Bcl-2. *Cellular immunology* 250: 31-39.
29. Tan, C., A. A. Taylor, M. Z. Coburn, J. H. Marino, C. J. Van De Wiele, and T. K. Teague. 2011. Ten-color flow cytometry reveals distinct patterns of expression of CD124 and CD126 by developing thymocytes. *BMC immunology* 12: 36.
30. Schmitt, T. M., and J. C. Zuniga-Pflucker. 2002. Induction of T cell development from hematopoietic progenitor cells by delta-like-1 in vitro. *Immunity* 17: 749-756.
31. Dinarello, C. A., D. Novick, S. Kim, and G. Kaplanski. 2013. Interleukin-18 and IL-18 Binding Protein. *Frontiers in immunology* 4: 289.
32. Huang, J., K. P. Garrett, R. Pelayo, J. C. Zuniga-Pflucker, H. T. Petrie, and P. W. Kincade. 2005. Propensity of adult lymphoid progenitors to progress to DN2/3 stage thymocytes with Notch receptor ligation. *Journal of immunology* 175: 4858-4865.
33. Massa, S., G. Balciunaite, R. Ceredig, and A. G. Rolink. 2006. Critical role for c-kit (CD117) in T cell lineage commitment and early thymocyte development in vitro. *European journal of immunology* 36: 526-532.
34. Zhou, J., J. Shang, J. Song, and F. Ping. 2013. Interleukin-18 augments growth ability of primary human melanocytes by PTEN inactivation through the AKT/NF-kappaB pathway. *The international journal of biochemistry & cell biology* 45: 308-316.
35. Takeda, K., H. Tsutsui, T. Yoshimoto, O. Adachi, N. Yoshida, T. Kishimoto, H. Okamura, K. Nakanishi, and S. Akira. 1998. Defective NK cell activity and Th1 response in IL-18-deficient mice. *Immunity* 8: 383-390.
36. Walsh, M. C., E. L. Pearce, P. J. Cejas, J. Lee, L. S. Wang, and Y. Choi. 2014. IL-18 Synergizes with IL-7 To Drive Slow Proliferation of Naive CD8 T Cells by Costimulating Self-Peptide-Mediated TCR Signals. *Journal of immunology*.
37. Iwai, Y., H. Hemmi, O. Mizenina, S. Kuroda, K. Suda, and R. M. Steinman. 2008. An IFN-gamma-IL-18 signaling loop accelerates memory CD8+ T cell proliferation. *PloS one* 3: e2404.
38. Billard, M. J., A. L. Gruver, and G. D. Sempowski. 2011. Acute endotoxin-induced thymic atrophy is characterized by intrathymic inflammatory and wound healing responses. *PloS one* 6: e17940.
39. Wang, S. D., K. J. Huang, Y. S. Lin, and H. Y. Lei. 1994. Sepsis-induced apoptosis of the thymocytes in mice. *Journal of immunology* 152: 5014-5021.
40. Gruver, A. L., and G. D. Sempowski. 2008. Cytokines, leptin, and stress-induced thymic atrophy. *Journal of leukocyte biology* 84: 915-923.
41. Moore, A. J., J. Sarmiento, M. Mohtashami, M. Braunstein, J. C. Zuniga-Pflucker, and M. K. Anderson. 2012. Transcriptional priming of intrathymic precursors for dendritic cell development. *Development* 139: 373-384.
42. Shah, D. K., and J. C. Zuniga-Pflucker. 2012. Notch receptor-ligand interactions during T cell development, a ligand endocytosis-driven mechanism. *Current topics in microbiology and immunology* 360: 19-46.
43. Gonzalez-Garcia, S., M. Garcia-Peydro, J. Alcain, and M. L. Toribio. 2012. Notch1 and IL-7 receptor signalling in early T-cell development and leukaemia. *Current topics in microbiology and immunology* 360: 47-73.
44. von Freeden-Jeffry, U., P. Vieira, L. A. Lucian, T. McNeil, S. E. Burdach, and R. Murray. 1995. Lymphopenia in interleukin (IL)-7 gene-deleted mice identifies IL-7 as a nonredundant cytokine. *The Journal of experimental medicine* 181: 1519-1526.
45. Maki, K., S. Sunaga, Y. Komagata, Y. Kodaira, A. Mabuchi, H. Karasuyama, K. Yokomuro, J. I. Miyazaki, and K. Ikuta. 1996. Interleukin 7 receptor-deficient mice lack gammadelta T cells. *Proceedings of the National Academy of Sciences of the United States of America* 93: 7172-7177.
46. Jahn, T., S. Sindhu, S. Gooch, P. Seipel, P. Lavori, E. Leifheit, and K. Weinberg. 2007. Direct interaction between Kit and the interleukin-7 receptor. *Blood* 110: 1840-1847.
47. Capitini, C. M., A. A. Chisti, and C. L. Mackall. 2009. Modulating T-cell homeostasis with IL-7: preclinical and clinical studies. *Journal of internal medicine* 266: 141-153.
48. Sasson, S. C., J. J. Zaunders, and A. D. Kelleher. 2006. The IL-7/IL-7 receptor axis: understanding its central role in T-cell homeostasis and the challenges facing its utilization as a novel therapy. *Current drug targets* 7: 1571-1582.
49. Chu, Y. W., S. A. Memon, S. O. Sharrow, F. T. Hakim, M. Eckhaus, P. J. Lucas, and R. E. Gress. 2004. Exogenous IL-7 increases recent thymic emigrants in peripheral lymphoid tissue without enhanced thymic function. *Blood* 104: 1110-1119.
50. Broers, A. E., S. J. Posthumus-van Sluijs, H. Spits, B. van der Holt, B. Lowenberg, E. Braakman, and J. J. Cornelissen. 2003. Interleukin-7 improves T-cell recovery after experimental T-cell-depleted bone marrow transplantation in T-cell-deficient mice by strong expansion of recent thymic emigrants. *Blood* 102: 1534-1540.
51. Goldberg, G. L., J. L. Zakrzewski, M. A. Perales, and M. R. van den Brink. 2007. Clinical strategies to enhance T cell reconstitution. *Seminars in immunology* 19: 289-296.
52. Srivastava, S., N. Salim, and M. J. Robertson. 2010. Interleukin-18: biology and role in the immunotherapy of cancer. *Current medicinal chemistry* 17: 3353-3357.
53. Tarhini, A. A., M. Millward, P. Mainwaring, R. Kefford, T. Logan, A. Pavlick, S. J. Kathman, K. H. Laubscher, M. M. Dar, and J. M. Kirkwood. 2009. A phase 2, randomized study of SB-485232, rhIL-18, in patients with previously untreated metastatic melanoma. *Cancer* 115: 859-868.
54. Simpkins, F., A. Flores, C. Chu, J. S. Berek, J. Lucci, 3rd, S. Murray, J. Bauman, H. Struemper, F. Germaschewski, Z. Jonak, O. Gardner, J. Toso, and G. Coukos. 2013. Chemoimmunotherapy using pegylated liposomal Doxorubicin and interleukin-18 in recurrent ovarian cancer: a phase I dose-escalation study. *Cancer immunology research* 1: 168-178.

What is claimed is:

1. A method of enhancing hematopoietic stem cell numbers in a subject in need of such therapy, comprising:
   injecting the subject intravenously with a quantity of bone marrow CD34+ hematopoietic stem cells; and
   administering to the subject an amount of interleukin-18 (IL-18) in combination with an amount of interleukin-7 (IL-7).

2. The method of claim 1, wherein the IL-18 and IL-7 are administered by at least one of subcutaneous, intravenous, intramuscular, and intraperitoneal injection.

3. A method of enhancing hematopoietic stem cell numbers in a subject in need of such therapy, comprising:
   injecting the subject intravenously with a quantity of bone marrow CD34+ hematopoietic stem cells; and
   administering to the subject via subcutaneous, intravenous, intramuscular, or intraperitoneal injection an amount of interleukin-18 (IL-18) in combination with an amount of interleukin-7 (IL-7).

* * * * *